(12) United States Patent
Wyatt

(10) Patent No.: US 6,957,218 B1
(45) Date of Patent: Oct. 18, 2005

(54) METHOD AND SYSTEM FOR CREATING A WEBSITE FOR A HEALTHCARE PROVIDER

(75) Inventor: Phil Wyatt, Highland Park, IL (US)

(73) Assignee: Medical Central Online, Lake Forest, IL (US)

( * ) Notice: Subject to any disclaimer, the term of this patent is extended or adjusted under 35 U.S.C. 154(b) by 0 days.

(21) Appl. No.: 09/544,510

(22) Filed: Apr. 6, 2000

(51) Int. Cl.[7] ............................................ G06F 17/30
(52) U.S. Cl. .................. 707/10; 707/102; 707/104.1; 715/501.1; 715/513; 709/203; 709/217; 709/219; 705/3
(58) Field of Search .............................. 707/1–10, 100, 707/102, 104, 203, 219; 709/203, 219, 217; 715/500.01; 705/3

(56) References Cited

U.S. PATENT DOCUMENTS

| | | | |
|---|---|---|---|
| 5,471,382 A | 11/1995 | Tallman et al. | |
| 5,517,405 A | 5/1996 | McAndrew et al. | |
| 5,544,044 A | 8/1996 | Leatherman | |
| 5,557,514 A | 9/1996 | Seare et al. | |
| 5,583,758 A | 12/1996 | McIlroy et al. | |
| 5,594,637 A | 1/1997 | Eisenburg et al. | |
| 5,664,109 A | 9/1997 | Johnson et al. | |
| 5,706,441 A | 1/1998 | Lockwood | |
| 5,724,379 A | 3/1998 | Perkins et al. | |
| 5,772,585 A * | 6/1998 | Lavin et al. | 600/300 |
| 5,793,972 A * | 8/1998 | Shane | 709/219 |
| 5,903,889 A * | 5/1999 | de la Huerga et al. | 707/3 |
| 5,915,240 A | 6/1999 | Karpf | |
| 5,918,208 A | 6/1999 | Javitt | |
| 5,924,073 A | 7/1999 | Tyuluman et al. | |
| 5,924,074 A | 7/1999 | Evans | |
| 5,940,802 A | 8/1999 | Hildebrand et al. | |
| 5,953,704 A | 9/1999 | McIlroy et al. | |
| 5,956,716 A * | 9/1999 | Kenner et al. | 707/10 |
| 5,964,700 A | 10/1999 | Tallman et al. | |
| 6,006,791 A | 12/1999 | Herrlein | |
| 6,014,630 A | 1/2000 | Jeacock et al. | |
| 6,035,276 A | 3/2000 | Newman et al. | |
| 6,038,566 A * | 4/2000 | Tsai | 707/102 |
| 6,076,166 A * | 6/2000 | Moshfeghi et al. | 707/9 |
| 6,088,677 A * | 7/2000 | Spurgeon | 705/4 |
| 6,148,297 A * | 11/2000 | Swor et al. | 707/3 |
| 6,148,298 A * | 11/2000 | LaStrange et al. | 707/10 |
| 6,151,581 A * | 11/2000 | Kraftson et al. | 705/3 |
| 6,195,651 B1 * | 2/2001 | Handel et al. | 707/2 |
| 6,202,062 B1 * | 3/2001 | Cameron et al. | 707/102 |
| 6,208,973 B1 * | 3/2001 | Boyer et al. | 705/4 |

(Continued)

OTHER PUBLICATIONS

"MedSeek's Wedsite Development Guide" from MedSeek, copyright 2001 (pps: 1-46).*

(Continued)

Primary Examiner—Jean M. Corrielus
Assistant Examiner—Anh Ly
(74) Attorney, Agent, or Firm—Patents+TMS, PC.

(57) ABSTRACT

A method and a system for creating websites for healthcare providers contained on a network are provided. Specifically, a healthcare provider such as, for example, a hospital, a nursing home, a practitioner and/or any other healthcare provider, may access a remote server and may create a website based on pre-defined information contained on the database. The website may then be stored on the remote server and may be searchable via a search engine on the remote server. In addition, the healthcare provider may associate a plurality of attributes to the website created so that a search engine may easily search for the healthcare provider based on the attributes associated therewith.

21 Claims, 1 Drawing Sheet

U.S. PATENT DOCUMENTS

| | | | |
|---|---|---|---|
| 6,266,668 B1 * | 7/2001 | Vanderveldt et al. | 707/10 |
| 6,270,455 B1 * | 8/2001 | Brown | 600/300 |
| 6,272,468 B1 * | 8/2001 | Melrose | 705/2 |
| 6,278,999 B1 * | 8/2001 | Knapp | 707/9 |
| 6,283,761 B1 * | 9/2001 | Joao | 434/236 |
| 6,308,171 B1 * | 10/2001 | De La Huerga | 707/3 |
| 6,330,426 B2 * | 12/2001 | Brown et al. | 434/307 R |
| 6,334,778 B1 * | 1/2002 | Brown | 434/258 |
| 6,343,271 B1 * | 1/2002 | Peterson et al. | 705/2 |
| 6,385,589 B1 * | 5/2002 | Trusheim et al. | 705/2 |
| 6,421,675 B1 * | 7/2002 | Ryan et al. | 707/100 |
| 6,493,724 B1 * | 12/2002 | Cusack et al. | 707/104.1 |
| 6,542,905 B1 * | 4/2003 | Fogel et al. | 707/200 |
| 6,560,639 B1 * | 5/2003 | Dan et al. | 707/10 |
| 6,587,829 B1 * | 7/2003 | Camarda et al. | 705/3 |
| 6,611,846 B1 * | 8/2003 | Stoodley | 707/104.1 |
| 6,654,749 B1 * | 11/2003 | Nashed | 707/10 |
| 6,658,431 B1 * | 12/2003 | Norman, Jr. | 707/104.1 |
| 6,738,754 B1 * | 5/2004 | Norman, Jr. | 707/2 |
| 6,757,898 B1 * | 6/2004 | Ilsen et al. | 709/203 |
| 6,769,018 B2 * | 7/2004 | Gagnon | 709/218 |
| 2001/0034757 A1 * | 10/2001 | Crockett | 709/203 |
| 2001/0041992 A1 * | 11/2001 | Lewis et al. | 705/3 |
| 2001/0043232 A1 * | 11/2001 | Abbott et al. | 345/700 |
| 2001/0054155 A1 * | 12/2001 | Hagan et al. | 713/193 |
| 2002/0007285 A1 * | 1/2002 | Rappaport | 705/2 |
| 2002/0010594 A1 * | 1/2002 | Levine | 705/2 |
| 2002/0010597 A1 * | 1/2002 | Mayer et al. | 705/2 |
| 2002/0194270 A1 * | 12/2002 | Gagnon | 709/203 |
| 2003/0208454 A1 * | 11/2003 | Rienhoff et al. | 707/1 |

OTHER PUBLICATIONS

Joyce Flory—"Supplemental Handout One: E-Health Colloquium" copyright Aug. 20, 2000 (pps: 1-50).*

* cited by examiner

METHOD AND SYSTEM FOR CREATING A WEBSITE FOR A HEALTHCARE PROVIDER

BACKGROUND OF THE INVENTION

The present invention generally relates to a method and a system for creating websites on a computer network. Specifically, the present invention relates to a method and a system for creating websites on a remote computer via a remote server using pre-defined information contained on a database within the remote server. A user of the remote computer may access the remote server via a computer network, such as, for example, the internet. Specifically, the method and the system allow a healthcare provider to create a website using pre-defined information on the remote server via the remote computer and having information relating to the healthcare provider on the website.

It is, of course, generally known to create websites having information thereon for providing the information on a computer network, such as, for example, the internet. A user using a remote computer may access the information from the database. Generally, however, individuals who wish to create a website must have a working knowledge of hyper-text markup language (HTML) or an HTML editor for creating the website and, further, must store the website on a remote server having access to the computer network at all times.

Further, it is generally known to provide a website created on a remote server whereby an individual may access the remote server and create a website using information contained on the remote server. Known websites that may provide these services are My Yahoo, Homestead.com and Salu.net.

However, known systems for creating websites on a remote server by accessing a remote server via a remote computer on a computer network do not allow healthcare providers, such as, for example, healthcare practitioners, hospitals, nursing homes, and other like facilities, to use pre-defined information related to the healthcare provider on the remote server for building a website related to the healthcare provider. Further, known systems do not provide such users the ability to subsequently store the website in a database on the remote server to provide for later search activities by a site visitor.

Moreover, a healthcare provider that may build a website to be placed on the internet must use "metatags" for specifically identifying the website within the computer network for allowing search engines to search the computer network for the websites. Site visibility for a website is, therefore, generally random and requires constant metatag management to be placed at the top of a search result list. Further, if a person wishes to find a healthcare provider on the internet, he must know the exact site address or find the website by chance using a search engine.

A need, therefore, exists for an improved method and a system for providing a searchable network having a plurality of websites relating to healthcare providers stored on a database within the network that overcome the problems associated with known methods and systems.

SUMMARY OF THE INVENTION

The present invention generally relates to a method and a system for providing a network on a remote server for storing websites of healthcare providers. Specifically, the present invention relates to a method and a system for allowing healthcare providers to create websites for storage within the network and subsequent updating of a search engine database.

To this end, in an embodiment of the present invention, a method is provided for creating websites for individuals, healthcare facilities and other healthcare providers. The method comprises the steps of: providing a remote server having a database; accessing the remote server via a first remote computer on a computer network; creating a website having a first web page by the remote computer on the remote server wherein the website relates to a healthcare provider providing healthcare services; assigning pre-defined attributes to the website that uniquely identify the website; and linking the website to the database wherein the database is searchable via a search engine wherein the search engine searches the database for specific attributes.

In an embodiment, the database is searched for the specific attributes.

In an embodiment, an update button is created on the website for instantly amending the database whenever the update button is chosen by the healthcare provider.

In an embodiment, the pre-defined attributes are stored on the database for recall of the attributes for placement in the website and related searchable attributes in the database.

In an embodiment, a plurality of databases is networked for storing the websites.

In an embodiment, the remote server is accessed for recalling the website stored on the database.

In an embodiment, links are added to the website for linking other websites relating to other healthcare providers to the website.

In an embodiment, photographs, various graphics and/or logos are added to the website via the remote computer.

In an embodiment, the website is associated with one or more practitioners who practice at or are involved with a practice, clinic, hospital, healthcare facility or other provider.

In an embodiment, one or more web pages are created on the website having information thereon related to any healthcare provider associated with the practice location.

In an embodiment, the database is accessed via a second remote computer. The database searches for the attributes of the website and the practitioner's individual website.

In an embodiment, pre-defined information is chosen to add to the website wherein the information uniquely identifies the website for searching of the database for the pre-defined website information.

In an embodiment, a plurality of web pages is added to the website related to the healthcare provider.

In an embodiment, the attributes are organized into files for storage within the database, and the files are searched via a search engine for at least one of the attributes stored within the database.

In another embodiment of the present invention, a system is provided for creating websites for healthcare providers. The system has a remote server having a database therein on a computer network. A first remote computer is connected to the remote server via the computer network wherein a website having a web page is created on the remote server via the remote computer using pre-defined information contained on the remote server wherein the website relates to a first healthcare provider providing healthcare services and further wherein the website is stored on the database. Pre-defined attributes are associated with the website for uniquely identifying the website in the database.

In an embodiment, an update button is provided on the website for instantly amending the website via the remote computer.

In an embodiment, an update button is provided on the website for instantly amending the searchable website attributes contained in the search engine database.

In an embodiment, a search engine is provided on the remote server for searching the database for the website via the attributes.

In an embodiment, a plurality of databases are networked together for storing and accessing the website.

In an embodiment, a second remote computer is provided wherein the second remote computer accesses the website.

In an embodiment, links on the website are provided for linking other websites to the website.

It is, therefore, an advantage of the present invention to provide a method and a system for creating websites for healthcare providers on a network that allow healthcare providers to create the websites related to the healthcare providers.

A further advantage of the present invention is to provide a method and a system for creating websites for healthcare providers within a network that stores websites within a database.

Moreover, an advantage of the present invention is to provide a method and a system for creating websites for healthcare providers within a network that allow attributes to be identified with the websites for searching the database for the attributes.

Still further, an advantage of the present invention is to provide a method and a system for creating websites for healthcare providers within a network that allow instant updating of the website attributes via a remote computer.

And, another advantage of the present invention is to provide a method and a system for creating websites for healthcare providers within a network that provide pre-defined information relating to the healthcare providers in the database for adding to the websites.

In addition, an advantage of the present invention is to provide a method and a system for creating websites for healthcare providers within a network that allow individuals to search the network for specific websites.

Still further, an advantage of the present invention is to provide a method and a system for creating websites for healthcare providers within a network that allow a plurality of healthcare providers to associate with each other on the network.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention relates to a method and a system for creating websites for healthcare providers contained on a network. More specifically, the present invention relates to a method and a system for creating websites for healthcare providers whereby a healthcare provider may create a website using pre-defined information relating to the healthcare provider contained on a database and then store the website on the database. An individual who accesses the database may search the database for the healthcare provider's website.

Figure 1:
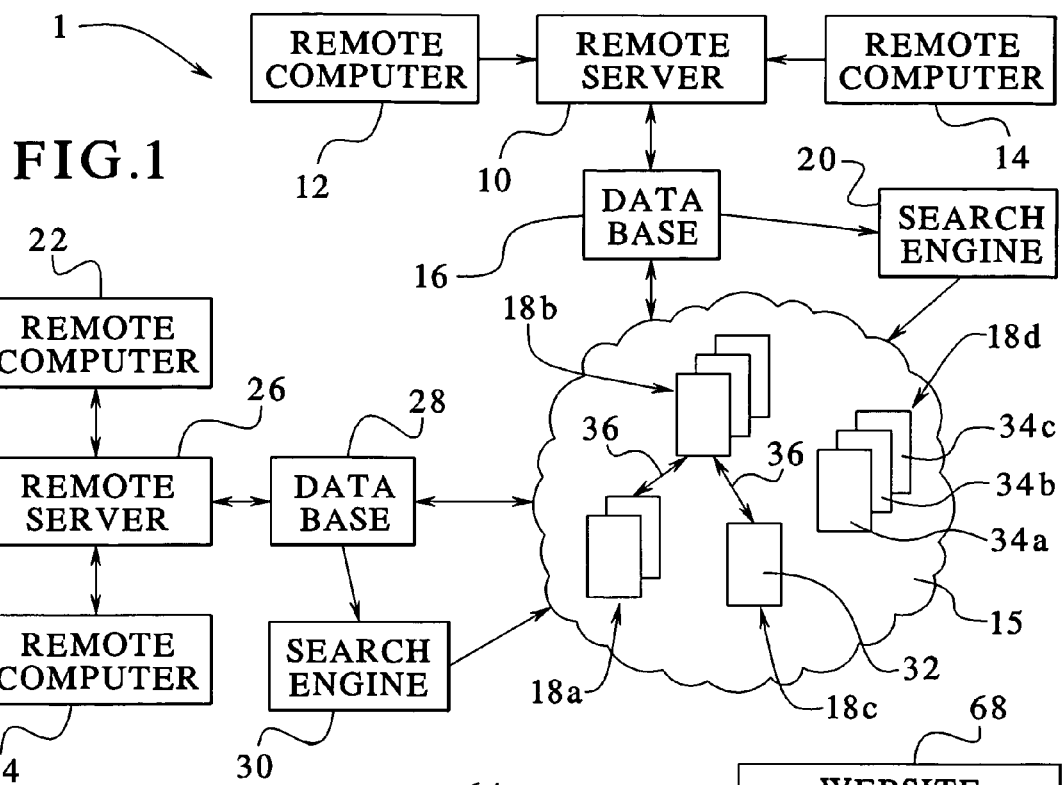
FIG. 1 illustrates a network contained between remote servers in an embodiment of the present invention.

Referring now to the drawings wherein like numerals refer to like parts, FIG. 1 illustrates a system 1 that may include a remote server 10 connected by remote computers 12,14. The remote server 10 may be connected to a global computer network such as, for example, the internet. Alternatively, the remote server 10 may be connected to an intranet such as, for example, within a corporation or a business such as on a LAN network. The remote computers 12,14 may have access to the remote server 10 via the computer network. The remote server 10 may have a database 16 contained therein and may store a plurality of websites 18a–18d within the database 16. A search engine 20 may be contained within the remote server 10 to search the websites 18a–18d.

Moreover, remote computers 22,24 may be attached to another remote server 26 that may have a database 28 contained therein. The database 28 may be connected with the database 16 to provide a network 15 for storing the websites 18a–18d and providing access to websites 18a–18d. In addition, the remote server 26 any include a search engine 30 that may search the database 28 or the database 16 to find one of the websites 18a–18d.

Any of the remote computers 12,14,22 and/or 24 may be wireless whereby the network 15 may be accessed from a remote location. For example, any of the computers 12, 14, 22 and/or 24 may be a Palm Pilot™ device by 3Com, Inc., or a wireless telephone that may access the internet wirelessly. It should be noted that any number of remote computers may be utilized in the network and the invention should not be construed as limited as herein described. Further, as indicated above, any number of remote servers may be connected having a plurality of databases to create the network 15 to store the websites 18a–18d. Still further, any number of websites may be contained within the databases 16,28 that may be apparent to those skilled in the art.

Further, the remote servers 10,26 or other remote server connected to the databases 16,28 and/or other databases may provide a distinct and unique portal for entry to the network 15. Therefore, an individual using the network 15 may have access to any and/or all of the websites contained on the network 15. Generally, the network 15 may be a self-contained network within the larger context of a large computer network, such as, for example, the internet.

Figure 2:
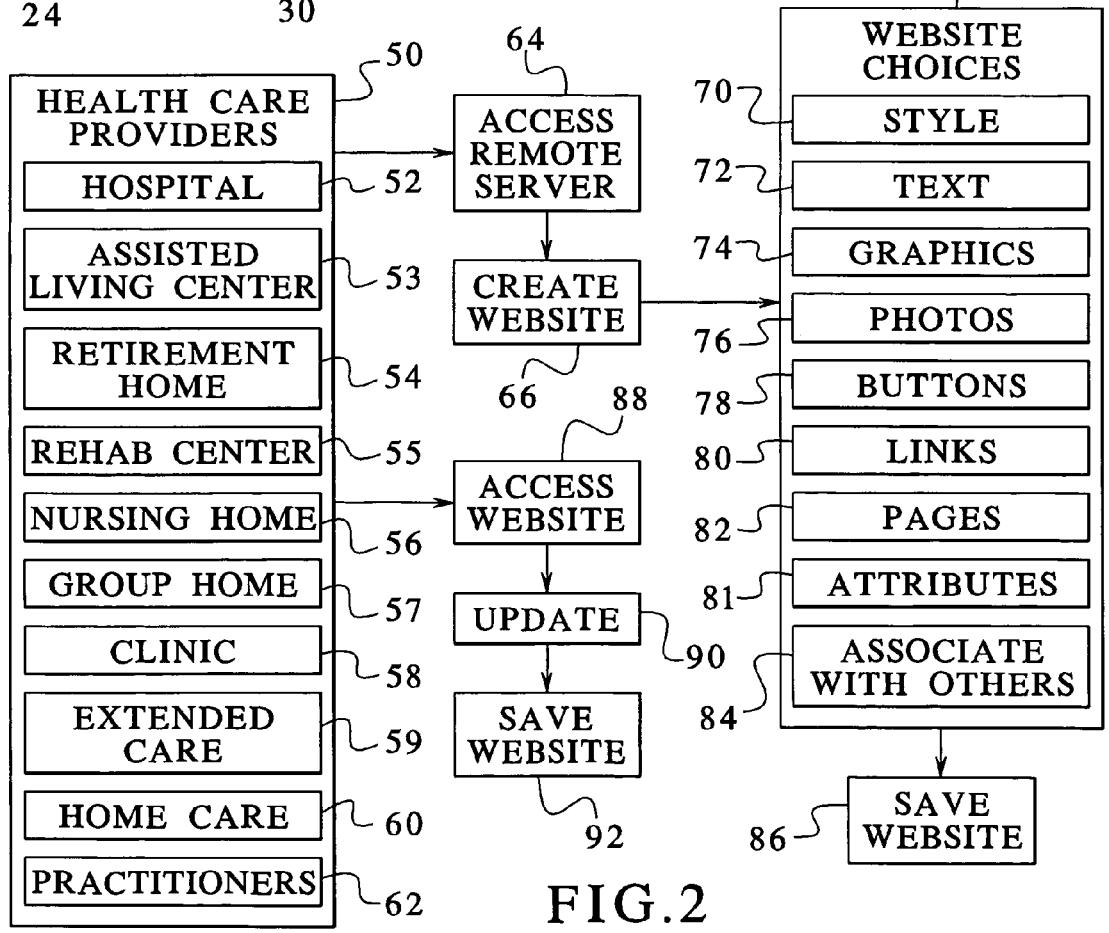
FIG. 2 illustrates a blackbox diagram showing a method for creating a website in an embodiment of the present invention.

Generally, a user of the system 1 such as, for example, a healthcare provider (as shown in FIG. 2) may access the remote server 10 via the remote computer 12. Upon accessing the remote server 10, the user may then create a website using materials stored within the database 16 such as, for example, pre-defined information relating to the healthcare provider such as, for example, text boxes, buttons, links, photographs, graphics or any other information that may be apparent to those skilled in the art. Further, the user may input distinctive information for placement on the website. The created website may be stored within the database 16 and may be accessed via any other remote computer by an individual wishing to contact, for example, the healthcare provider. Further, the individual may wish to search for the healthcare provider within the database 16 via the search engines 20,30 or any other search engine apparent to those skilled in the art.

Each of the websites 18a–18d or any other website that may be stored in the databases 16,28, may consist of a single web page 32 as illustrated by the website 18c. Alternatively, the websites may consist of a plurality of web pages 34a–34c as shown by the website 18d. Any number of web pages may be created for each of the websites 18a–18d or any other website that may contain information related to the health care provider. Links may be provided on each web page for access to the web pages on each of the websites.

Further, a website created by one of the healthcare providers may be associated with another website of another healthcare provider or a plurality of healthcare providers via associations 36. For example, a health care provider such as, for example, a dentist may create a website 18a relating information about the dentist. Further, an orthodontist may create a website 18b relating information about the orthodontist. The dentist and the orthodontist may wish to associate themselves together for referrals of patients. A link may be provided on each of the websites 18a,18b thereby linking the websites 18a,18b to each other.

Referring now to FIG. 2, a plurality of healthcare providers 50 is shown. The plurality of healthcare providers 50 may include a hospital 52, an assisted living center 53, a retirement home 54, a rehabilitation center 55, a nursing home 56, a group home 57, a clinic 58, an extended care center 59, a home care provider 60 and/or a practitioner 62. Further, any other healthcare provider may be included within the plurality of healthcare providers 50 that may be apparent to those skilled in the art.

Any of the plurality of healthcare providers 50 may access the remote server 10 or 26 via step 64 and create a website via step 66. The remote server may show a form on a web page that may be accessed via a web browser such as, for example, Netscape or Internet Explorer. The form may include a plurality of choices 68 for the healthcare provider to design the website. The website choices may include a choice of styles 70, text 72, graphics 74, photos 76, buttons 78, links 80, attributes 81, pages 82 or associations with others 84. Each of the website choices 68 may be stored within the databases 16,28 to be chosen by the healthcare provider creating the website for placement on the website of the healthcare provider.

The style choice 70 may include an ability to change the presentation of the look of the website. This may include how items on the website are arranged, colors that are used, and other aspects of the website relating to the overall look of the website. The text choice 72 may include the ability to create text boxes on the website to fill with text that may relate to the healthcare provider. The text choice 72 may allow an individual that accesses the site to gain information regarding the healthcare provider or for any other reason that may be apparent to those skilled in the art.

The graphics choice 74 may allow a healthcare provider to add graphics to the website to make the website more appealing, attractive and/or informative. The graphics may be saved within the database 16 or 28 or in any other database. Further, graphics 74 may be imported to the website via the remote computer 12 by the healthcare provider. This may allow the healthcare provider to input graphics relating to that particular healthcare provider. Photos 76 may also be added to the website. The photos 76 may be imported into the website by the healthcare provider or may be taken from the databases 16,28.

Further, buttons 78 may be provided that may transport the user to another place on the network such as, for example, to another page or to another website. Further, links 80 may be provided that also may transport an individual to other pages 82 or other websites contained within the network.

The healthcare provider may associate with others 84 by linking the website of the healthcare provider with websites from other healthcare providers contained within the network. This may allow an individual searching the network to find other healthcare providers that may be recommended by the healthcare provider on the website the individual is viewing.

A plurality of attributes 81 may be contained within the databases 16,28 that may uniquely describe the health care providers creating the website. These attributes may include location, names of personnel, amenities, services, treatments, specialities, care philosophy, hours, diseases treated or any other attribute that may be apparent to those skilled in the art. The attributes 81 may be chosen by the health care provider via an attribute list for placement of the information on the website. The attributes 81 may allow an individual to search the databases 16,28 via the search engines 20,30 to find a website or a plurality of websites having the same or similar attributes to what is desired by the individual conducting the search.

Further, other website choices 68 may be provided that may allow the healthcare provider to create a unique and informative website. After the healthcare provider has created the website, the healthcare provider may save the website via step 86 on the database 16 or 28 or any other database. Therefore, the website created by the healthcare provider via the remote computer 12 may be contained on the network 15 of databases 16,28 or any other database.

Alternatively, the healthcare provider may access the website of the healthcare provider via step 88. Each of the websites created by the healthcare providers 50 may automatically contain an update button 90 that may allow the healthcare provider to have instant access to changing the website of the healthcare provider. The healthcare provider may add information to the website, may change links associated with the website or may do any other editing of the website that may be apparent to those skilled in the art. After the healthcare provider has updated the website of the healthcare provider, the healthcare provider may save the website within the databases 16,28 via step 92.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A computer-implemented method for creating websites for one of a plurality of healthcare providers, the method comprising the steps of:

providing a remote server having a database;

accessing the remote server via a first remote computer on a computer network;

accessing a form in the database via the first remote computer on the computer network wherein the form includes pre-defined information and pre-defined attributes wherein the pre-defined attributes are characteristics of the plurality of healthcare providers;

selecting the pre-defined information from the form wherein the pre-defined information describes one of the plurality of healthcare providers;

selecting one of the pre-defined attributes from the form wherein one of the pre-defined attributes corresponds to healthcare services provided by one of the plurality of healthcare providers;

creating a website having a first web page by the first remote computer on the remote server wherein the website identifies one of the plurality of healthcare providers providing the healthcare services;

editing a presentation of the website wherein one of the plurality of healthcare providers selects a preference from the remote server via the first remote computer wherein the presentation of the website is based on the preference and further wherein the preference relates to one of a style of the website, a text of the website or a graphic of the website;

designing the first web page of the website wherein the pre-defined information and one of the pre-defined attributes on the first web page of the website are arranged on the first web page by one of the plurality of healthcare providers via the first remote computer; and linking the website to the database wherein the database is searchable via a search engine wherein the search engine searches the database for specific attributes wherein one of the specific attributes corresponds to one of the pre-defined attributes.

2. The method of claim 1 further comprising the step of:
searching the database for the specific attributes.

3. The method of claim 1 further comprising the step of:
creating an update button on the website for instantly amending the database when the update button is chosen by one of the plurality of healthcare provider.

4. The method of claim 1 further comprising the step of:
storing the pre-defined attributes on the database for recall of the pre-defined attributes for placement on the website.

5. The method of claim 1 further comprising the step of:
networking a plurality of databases for storing the website.

6. The method of claim 1 further comprising the step of:
accessing the remote server for recalling the website stored on the database.

7. The method of claim 1 further comprising the step of:
adding links to the website for linking other websites relating to other healthcare providers to the website.

8. The method of claim 1 further comprising the step of:
adding one or more photographs, graphics and logos to the website via the remote computer.

9. The method of claim 1 further comprising the step of:
associating the website with one or more practitioners who practice at least one of a practice, a clinic, a hospital or a healthcare facility.

10. The method of claim 1 further comprising the step of:
creating one or more web pages on the website having information thereon related to a practice location of one of the plurality of healthcare provider.

11. The method of claim 1 further comprising the steps of:
accessing the database via a second remote computer;
searching the database for the pre-defined attributes of the website; and
displaying the website.

12. The method of claim 1 further comprising the steps of:
choosing pre-defined information to add to the website wherein the pre-defined information uniquely identifies the website to search the website for the pre-defined information.

13. The method of claim 1 further comprising the step of:
adding a plurality of web pages to the website related to one of the healthcare providers.

14. The method of claim 1 further comprising the step of:
organizing the pre-defined attributes into files for storage within the database; and
searching the files via a search engine for at least one of the pre-defined attributes stored within the database.

15. A computer-implemented creating websites for healthcare providers, the system comprising:
a remote server having a database therein wherein the database is accessible by a computer network;
a first remote computer connected to the remote server via the computer network wherein a website having a web page is created on the remote server via the remote computer using pre-defined information contained on the remote server wherein the pre-defined information corresponds to one of healthcare providers wherein the pre-defined information describes amenities of one of the healthcare providers and identifies a location of one of the healthcare providers wherein the web page is created with the pre-defined information and further wherein the website is stored on the database;
a list of design choices in the database wherein one of the healthcare providers selects a design choice from the list of design choices wherein the design choice effects a presentation of the web page of the website and further wherein the design choice relates a style of the web page, a text, a graphic, a photograph or a link from the website; and
a list of pre-defined attributes in the database wherein one of the pre-defined attributes is selected from the list of pre-defined attributes wherein the pre-defined attributes identify healthcare services of the healthcare providers wherein one of the healthcare providers arranges the pre-defined information and one of the pre-defined attributes on the web page of the website via the remote computer.

16. The system of claim 15 further comprising:
an update button on the website for instantly amending the website via the remote computer.

17. The system of claim 15 further comprising:
an update button on the website for instantly amending the pre-defined attributes contained in the database.

18. The system of claim 15 further comprising:
a search engine on the remote server for searching the database for the website via the pre-defined attributes.

19. The system of claim 15 further comprising:
a plurality of databases networked together for storing and accessing the website.

20. The system of claim 15 further comprising:
a second remote computer wherein the second remote computer accesses the website.

21. The system of claim 15 further comprising:
links on the website for linking other websites to the website.

* * * * *